(12) United States Patent
Raths et al.

(10) Patent No.: US 6,235,913 B1
(45) Date of Patent: May 22, 2001

(54) METHOD FOR PRODUCING FATTY ACID POLYGLYCOL ESTER SULPHATES

(75) Inventors: Hans-Christian Raths, Monheim; Thomas Engels, Duesseldorf; Rainer Rueben, Monheim; Joerg Kahre, Leichlingen, all of (DE)

(73) Assignee: Cognis Deutschland GmbH, Duesseldorf (DE)

( * ) Notice: Subject to any disclaimer, the term of this patent is extended or adjusted under 35 U.S.C. 154(b) by 0 days.

(21) Appl. No.: 09/486,413

(22) PCT Filed: Aug. 17, 1998

(86) PCT No.: PCT/EP98/05209

§ 371 Date: May 22, 2000

§ 102(e) Date: May 22, 2000

(87) PCT Pub. No.: WO99/10319

PCT Pub. Date: Mar. 4, 1999

(30) Foreign Application Priority Data

Aug. 5, 1997 (DE) .............................. 197 36 906

(51) Int. Cl.$^7$ ....................................... C11D 1/28
(52) U.S. Cl. ................. 554/98; 554/97; 516/200
(58) Field of Search ................. 584/98, 97; 516/200

(56) References Cited

U.S. PATENT DOCUMENTS 3,884,946  5/1975  Sung et al. .
5,304,664  4/1994  Peppmoeller et al. .
5,391,782  2/1995  Colignon et al. .

FOREIGN PATENT DOCUMENTS 2 024 050    12/1971  (DE) .
40 17 463 A1 12/1991  (DE) .
0 366 015     5/1990  (EP) .

OTHER PUBLICATIONS

K. Engel, et al.: "Darstellung und Eigenschaften von Fettsaeurepolyglycolestersulfaten", Fette, Seifen, Anstrichmittel, vol. 88, Jan., 1986, pp. 20–25.

Primary Examiner—Deborah D. Carr
(74) Attorney, Agent, or Firm—John E. Drach; Aaron R. Ettelman

(57) ABSTRACT

A method of producing fatty acid polyglycol ester sulfates of the general formula (I):

$$R^1COO(AO)_nSO_3M \quad (I)$$

is disclosed, wherein $R^1CO$ represents a linear or branched, aliphatic, saturated and/or unsaturated acyl radical with 6 to 22 carbon atoms, AO represents $CH_2CH_2O$, $CHCH_3CH2O$ and/or $CH_2CHCH_3$, n represents a number from about 0.5 to about 5 and M represents a cation. The disclosed process comprises the sulfation of fatty acid polyglycol esters followed by neutralization, wherein the neutralization is carried out at a pH of from about 5 to about 9.

20 Claims, No Drawings

METHOD FOR PRODUCING FATTY ACID POLYGLYCOL ESTER SULPHATES

CROSS-REFERENCE TO RELATED APPLICATIONS

This application is a 35 U.S.C. §371 national stage application based upon International Application No. EP98/05209, filed on Aug. 17, 1998.

BACKGROUND OF THE INVENTION

For some time, fatty acid polyethylene glycol esters, more particularly fatty acids with a low degree of ethoxylation, such as fatty acid +1EO adducts, have been described in the literature as interesting intermediates for the synthesis of ether sulfate surfactants with an isethionate-like structure. At first, however, difficulties were involved in producing the fatty acid polyethylene glycol esters used as starting compounds in satisfactory selectivities. Apart from the unwanted percentage of relatively highly ethoxylated homologs, significant quantities of polyethylene glycol and diesters were also formed by the relatively old known processes. Only recently has it been possible to produce fatty acids with low degrees of ethoxylation in yields of more than 90% of the theoretical by using special alkanolamines as ethoxylation catalysts. Apart from the fact that it was already difficult enough to provide the starting compounds in suitable qualities, the sulfation of these compounds also presented considerable difficulties. Although, according to the article by K. Engel and W. Rubak in Fette, Seifen, Anstrichm., 88, 20 (1986), sulfated fatty acid polyethylene glycol esters can be obtained by reacting fatty acid polyglycol esters with chlorosulfonic acid in methylene chloride, only traces of anionic surfactants could be detected after neutralization under standard conditions. In other words, the mixture left after neutralization contained hardly any more anionic sulfated fatty acid polyethylene glycol esters, but mainly hydrolysis products, such as fatty acids, soaps, short-chain glycol monosulfates and glycol disulfates. Better results were obtained when the neutralization step was carried out at temperatures of 0 to −20° C. However, a process such as this would be unsuitable for industrial-scale production because, on the one hand, methylene chloride is used as solvent and would have to be removed in a separate working-up step and, on the other hand, cooling for working temperatures below 0° C. would only be possible on an industrial scale at enormous cost.

Accordingly, the problem addressed by the present invention was to provide an improved process for the sulfation of fatty acids, especially fatty acids with a low degree of alkoxylation, which could be used on an industrial scale to provide fatty acid polyglycol ester sulfates without any further working up.

BRIEF SUMMARY OF THE INVENTION

The present invention includes a process for the production of fatty acid polyglycol ester sulfates by sulfation of fatty acid polyglycol esters and subsequent neutralization and to their use as foam boosters, especially for surfactant mixtures containing nonionic surfactants.

The present invention relates to a process for the production of fatty acid polyglycol ester sulfates corresponding to formula (I):

$$R^1COO(AO)_nSO_3M \qquad (I)$$

in which $R^1CO$ is a linear or branched, aliphatic, saturated and/or unsaturated acyl group containing 6 to 22 carbon atoms, AO stands for $CH_2CH_2O$, $CHCH_3CH_2O$ and/or $CH_2CHCH_3O$, n is a number of 0.5 to 5 and M is a cation, by sulfation of fatty acid polyglycol esters and subsequent neutralization, characterized in that the entire neutralization step is carried out at a pH value of 5 to 9.

It has surprisingly been found that, by carrying out the neutralization step under the described conditions, fatty acid polyglycol ester sulfates are obtained in high yields and the problem of hydrolysis is reliably avoided.

DETAILED DESCRIPTION OF THE INVENTION

Fatty Acid Polyglycol Esters

The sulfation products are produced from fatty acid polyglycol esters corresponding to formula (II):

$$R^1COO(AO)_nH \qquad (II)$$

in which $R^1CO$ is a linear or branched, aliphatic, saturated and/or unsaturated acyl group containing 6 to 22 carbon atoms, AO stands for $CH_2CH_2O$, $CHCH_3CH_2O$ and/or $CH_2CHCH_3$ and n is a number of 0.5 to 5. The esters may be prepared by known methods of preparative organic chemistry, for example by addition of ethylene oxide and/or propylene oxide onto fatty acids in the presence of a base as homogeneous catalyst.

Fatty acids in the context of the invention are understood to be aliphatic carboxylic acids corresponding to the formula $R^1COOH$, in which $R^1CO$ is an aliphatic, linear or branched acyl group containing 6 to 22 and preferably 12 to 18 carbon atoms and 0 and/or 1, 2 or 3 double bonds. Typical examples are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils, in the reduction of aldehydes from Roelen's oxosynthesis or as monomer fraction in the dimerization of unsaturated fatty acids. Technical fatty acids containing 12 to 18 carbon atoms, for example coconut, palm, palm kernel or tallow fatty acid, are preferred. Accordingly, $R^1CO$ in formulae (I) and (II) is preferably an acyl group containing 12 to 18 carbon atoms.

Alkoxylation

Suitable basic catalysts for the alkoxylation step are both alkanol-amines, such as monoethanolamine, diethanolamine and preferably tri-ethanolamine, and the amines described in DE 2024050 AS, such as mono-, di- and trimethylamine, mono-, di- and triethylamine, mono-, di- and tri-n-butylamine, tertbutylamine, mono-, di- and tripropylamine, diisopropyl-amine, n-hexylamine, n-dodecylamine, N,N-dimethyl-n-dodecylamine, N,N-dimethyloctadecylamine, docosylamine, hexamethylenediamine, N,N,N', N'-tetramethyl hexamethylenediamine, tetraethylene pentamine, triethylene-diamine, cyclohexylamine, aniline, benzylamine, hexamethylenetetramine, diethylenetriamine, N,N-dimethyl aniline, methoxyanilines and morpholine. The described alkanolamines are particularly preferred catalysts. The alkanolamines are used in quantities of normally 0.1 to 5% by weight and preferably 0.5 to 1.5% by weight, based on the fatty acids. The alkoxylation step may be carried out in known manner. The fatty acid and the catalyst are normally introduced into a stirred autoclave from which traces of water are removed before the reaction by alternate evacuation and purging with nitrogen. The fatty acid is then reacted with ethylene oxide and/or propylene oxide in a molar ratio of 1:0.5 to 1:5 and preferably 1:1 to 1:2 which may be introduced into the pressure vessel in portions via a siphon after heating. Accordingly, the index n in formulae (I) and (II) is a number of 0.5 to 5 and preferably a number of 1 to 2. The alkoxylation may be carried out at temperatures of 80 to 180° C. and preferably 100 to 120° C. under autogenous pressures of 1 to 5 bar and preferably 2 to 3 bar. On completion of the reaction, it is advisable to stir the reaction mixture for a certain time (15 to 90 mins.) at the reaction temperature in order to complete the reaction. The autoclave is then cooled and vented and, if desired, acids, for example lactic acid or phosphoric acid, are added to the product in order to neutralize the basic catalyst. According to the invention, both ethoxylated or propoxylated or even ethoxylated and propoxylated fatty acids may be used as starting compounds. If ethoxylated and pro-poxylated fatty acids are used, they may be random or even block compounds. In the case of the mixed-alkoxylated fatty acids, the ratio of ethylene oxide to propylene oxide to be used may be varied within wide limits as long as, overall, the degree of alkoxylation n is in the range mentioned above. However, the consistency of the alkoxylated fatty acid can be influenced through the percentage content of propylene oxide. Thus, the softening temperature of the alkoxylated fatty acids becomes lower with increasing degree of propoxylation. If the fatty acids are exclusively propoxylated, liquid products are actually obtained whereas fatty acids which have been exclusively ethoxylated represent solid compounds.

Sulfation

In one embodiment, the sulfation of the fatty acid alkylene glycol esters may be carried out with gaseous sulfur trioxide by the known method for sulfating fatty acid lower alkyl esters, continuous reactors operating on the falling-film principle being preferred. The sulfur trioxide is diluted with an inert gas, preferably air or nitrogen, and used in the form of a gas mixture which contains the sulfur trioxide in a concentration of 1 to 8% by volume and more particularly 2 to 5% by volume. The molar ratio of fatty acid alkylene glycol ester to sulfur trioxide is generally 1:1 to 1:1.3 and preferably 1:1.05 to 1:1.1. The sulfation reaction is preferably carried out in a continuous falling-film reactor at temperatures at least 5 to 10° C. above the melting point of the fatty acid alkylene glycol ester. In general, the sulfation temperatures are up to at most 30° C. above the melting point of the fatty acid alkylene glycol esters. In another embodiment of the invention, the sulfation reaction is carried out with a sulfating agent, more particularly chlorosulfonic acid. The reaction is carried out under conditions familiar to the expert, for example in a continuous process using substantially stoichiometric quantities of chlorosulfonic acid.

Neutralization

Now, it is crucial to the invention that the acidic esters of formula (I) obtained after the sulfation step are neutralized in known manner with bases and that the pH value is in the range from 5 to 9 and preferably in the range from 6 to 8 throughout the neutralization process. It has proved to be of advantage to carry out the neutralization by allowing the acidic ester to run into an aqueous solution, the pH of the aqueous solution being kept at a value of 5 to 9 by separately adding the alkaline solution intended for the neutralization step. On an industrial scale, this may be done by simultaneously adding the liquid acidic ester and the alkaline solution intended for neutralization to the neutralization circuit. One example of a suitable neutralization circuit is disclosed in DE 4017463 A1. In addition, it has been found to be of advantage to carry out the neutralization step at temperatures of 10 to 40° C. and preferably at temperatures of 20 to 35° C. However, any other neutralization process known to the expert, for example spray neutralization, may also be used as long as the pH value mentioned above is maintained for the neutralization process. Hydroxides, such as alkali metal hydroxide, alkaline earth metal hydroxide or even ammonia and/or water-soluble organic amines, such as mono-, di- and tri- $C_{2-4}$-alkanolamines, for example mono-, di- and triethanolamine, and primary, secondary or tertiary $C_{1-4}$ alkylamines, may be used for the neutralization step. The neutralization bases are preferably used in the form of 20 to 50% by weight aqueous solutions. Aqueous solutions of ammonia or sodium and/or potassium hydroxide are preferably used for the neutralization step, so that M in formula (I) is preferably a sodium, potassium or ammonium ion. More particularly, M is an ammonium ion because corresponding compounds of formula (I) show particularly favorable solubility behavior. After the neutralization step, the aqueous solutions of the sulfation products are preferably adjusted to pH values of 6 to 7. These solutions remain stable even after storage for several months at room temperature. If desired, the fatty acid polyglycol ester sulfates may then be bleached in known manner. Here, too, bleaching should be carried out at the pH values mentioned above. In addition, antimicrobial agents or even pH buffers may be added in quantities of up to 10% by weight, based on the active substance content of the sulfation products, in order to stabilize the aqueous preparations in storage.

Sulfation Products

The sulfation products typically have the following composition (based on the non-aqueous component):

(a) 40 to 98% by weight fatty acid alkylene glycol ester sulfates corresponding to formula (I), (b) 0.1 to 10% by weight glycol monosulfates and glycol disulfates, (c) 0.1 to 10% by weight fatty acid soaps, (d) 0.1 to 45% by weight unsulfated components, i.e. fatty acid polyglycol esters, and (e) 0.1 to 15% by weight inorganic sulfates, based on the mixture of solids.

The aqueous component is not critical and, typically, may be between 50 and 95% by weight.

Commercial Applications

According to the invention, it has also been found that the fatty acid polyglycol ester sulfates corresponding to formula (I) are excellent foam boosters for low-foaming surfactant mixtures either on their own or even in combination with one or more of the compounds described above under (b) to (e). Mixtures of the fatty acid polyglycol ester sulfates with non-sulfated starting materials are also particularly suitable. These preparations may be prepared by mixing or may even be formed in situ, for example by only partially completing the sulfation reaction. The low-foaming surfactant mixtures preferably contain nonionic surfactants. "Low-foaming" in the context of the present invention applies to surfactant mixtures which, in the rotor test described in Example 2, produce a foam volume of less than 500 ml after 3 minutes.

Nonionic Surfactants

Nonionic surfactants which may be present in the surfactant mixtures are fatty alcohol polyglycol ethers, alkylphenol polyglycol ethers, fatty acid amide polyglycol ethers, fatty amine polyglycol ethers, alkoxylated triglycerides, mixed ethers, polyol fatty acid esters, fatty acid polyethylene glycol esters, fatty acid methyl ester ethoxylates, sugar esters, sorbitan esters, polysorbates, acyl glucamides and alkyl polyglycosides. Surfactant mixtures containing alkyl polyglycosides are particularly susceptible to the problem that these mixtures are very slow in developing foam or show inadequate foam stabilities. This is particularly troublesome in the case of body-care products because the user expects surfactant mixtures to rapidly develop attractive stable foams. It has been found that surfactant mixtures containing alkyl polyglycosides do not have these disadvantages if sulfated fatty acid alkylene glycol esters are added either on their own or in combination with one or more of the compounds described under (b) to (e). Accordingly, the present invention also relates to the use of sulfated fatty acid polyalkylene glycol esters corresponding to formula (I) as foam boosters for low-foaming surfactant mixtures. The described compounds are preferably used as foam boosters for surfactant mixtures containing nonionic surfactants, more particularly for surfactant mixtures containing alkyl polyglycosides. The quantity of fatty acid polyglycol ester sulfate added may be between 0.1 and 5% by weight, based on the quantity of solids in the preparations.

Alkyl Polyglycosides

Alkyl polyglycosides in the context of the present invention are understood to be alkyl and alkenyl glycosides corresponding to formula (III):

RO-[G]$_p$ (III)

in which R is an alkyl and/or alkenyl group containing 4 to 22 carbon atoms, G is a sugar unit containing 5 or 6 carbon atoms and p is a number of 1 to 10. They may be obtained by the relevant methods of preparative organic chemistry. The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The index p in general formula (III) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view. The alkyl or alkenyl group R may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred. In addition, the alkyl or alkenyl radical R may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12/14}$ cocoalcohol with a DP of 1 to 3 are preferred.

Anionic, Cationic and/or Amphoteric Surfactants

The surfactant mixtures may of course contain other surfactants, for example anionic, cationic and/or amphoteric surfactants. Typical examples of anionic surfactants are alkyl benzenesulfonates, alkanesulfonates, olefin sulfonates, alkylether sulfonates, glycerol ether sulfonates, α-methyl ester sulfonates, sulfofatty acids, alkyl sulfates, fatty alcohol ether sulfates, glycerol ether sulfates, hydroxy mixed ether sulfates, monolyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethion-ates, fatty acid sarcosinates, fatty acid taurides, acyl lactylates, acyl tartrates, acyl glutamates, acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of cationic surfactants are quaternary ammonium compounds and esterquats, more particularly quaternized fatty acid trialkanolamine ester salts. Typical examples of amphoteric or zwitterionic surfactants are alkylbetaines, alkylamidobetaines, aminopropionates, aminoglycinates, imidazolinium betaines and sulfobetaines.

EXAMPLES

Example 1

200 g (1 mole) of technical lauric acid was introduced into a 1 liter stirred autoclave and 2 g of triethanolamine (corresponding to 1% by weight, based on lauric acid) were subsequently added. The autoclave was alternately evacuated and purged with nitrogen three times to remove traces of water which could lead to the formation of polyethylene glycol. After the reaction mixture had been purged with nitrogen for the last time, the autoclave was closed and heated to 100° C. and 44 g (1 mole) of ethylene oxide were introduced in portions up to a maximum pressure of 5 bar. On completion of the reaction, which was reflected in the fact that the pressure fell back to a value of 1.2 bar and then remained constant, the reaction mixture was stirred for 30 minutes and then cooled and vented. The basic catalyst was neutralized by adding the necessary quantity of lactic acid. The lauric acid +1EO adduct obtained was melted at 40° C. and sulfated with gaseous sulfur trioxide (dilution 3 to 5% in dried air) in a molar ratio of 1:1.1 at 40° C. in a falling-film reactor. The acidic ester obtained was neutralized at a temperature below 40° C. with an aqueous ammonia solution containing 1% by weight of triethanolamine, based on ammonia, by allowing the two solutions to run in together. The pH value was kept at 6 to 8 throughout. The solution was then adjusted to a pH of 6.5. The dried salt had the following composition:

Fatty acid polyglycol ester sulfate (anionic substance): 56.0% by weight

Glycol monosulfate and disulfate: 7.5% by weight
Lauric acid ammonium salt: 5.0% by weight
Ethylene glycol monoester and diester (unsulfonated components): 22.0% by weight
Ammonium sulfate: 9.5% by weight Example 2

1-Liter test solutions in water with a hardness of 15° dH were prepared (cf. Table 1). 200 ml of the test solutions were foamed for 3 minutes at 40° C. in the rotor test (1300 r.p.m.). In this test, air is stirred into the test solution by means of a special stirrer head so that the solution foams. In order to measure the initial foaming kinetics, i.e. the behavior of the foam in the initial period, the stirrer is switched off at intervals of 10 seconds for the first 90 seconds in order to read off the foam height and liquid level from the scale. The stirrer is then switched on again. To determine foam stability, the foam and liquid height after the total stirring time of 3 minutes is recorded for another 5 minutes. The initial foaming kinetics are calculated from the linear part of the gradients of the mean foam volumes determined at 10-second intervals over the first minute. They are expressed in ml/s. The results are set out in Table 1.

TABLE 1

Foam behavior (quantities in g)

| Composition/Performance | C1 | C2 | C3 | 1 | C4 |
|---|---|---|---|---|---|
| Lauric acid + 1EO sulfate sodium salt | 0.6 | — | — | 0.15 | — |
| Coco Glucosides | — | 0.6 | — | 0.6 | 0.6 |
| Sodium Laureth Sulfate | — | — | 0.6 | — | 0.15 |
| Sebum | | | 0.1 | | |
| Water | | | to 100 | | |
| Foam height [ml] | | | | | |
| -After 1 min. | 300 | 100 | 300 | 260 | 240 |
| -After 2 mins. | 760 | 210 | 780 | 530 | 480 |
| -After 3 mins. | 850 | 300 | 850 | 770 | 680 |
| -After 4 mins. | 800 | 240 | 800 | 700 | 550 |
| -After 6 mins. | 750 | 230 | 750 | 650 | 500 |
| -After 8 mins. | 730 | 230 | 730 | 630 | 480 |
| Initial foaming kinetics [ml/s] | 6.5 | 1.8 | 6.8 | 4.6 | 3.9 |

It can be seen that the fatty acid polyglycol ester sulfates produce better foaming kinetics for alkyl polyglycosides (Coco Glucosides) than ether sulfates (Sodium Laureth Sulfate) and also guarantee better foam behavior over a longer period.

What is claimed is:

1. A method of producing a fatty acid polyglycol ester sulfate of the general formula (I):

$$R^1COO(AO)_nSO_3M \quad (I)$$

wherein $R^1CO$ represents a linear or branched, aliphatic, saturated and/or unsaturated acyl radical with 6 to 22 carbon atoms, AO represents $CH_2CH_2O$, $CHCH_3CH2O$ and/or $CH_2CHCH_3O$, n represents a number from about 0.5 to about 5 and M represents a cation, said process comprising:
   (a) sulfating a fatty acid polyglycol ester of the general formula (II):

$$R^1COO(AO)_nH \quad (II)$$

wherein $R^1CO$ represents a linear or branched, aliphatic, saturated and/or unsaturated acyl radical with 6 to 22 carbon atoms, AO represents $CH_2CH_2O$, $CHCH_3CH2O$ and/or $CH_2CHCH_3O$, and n represents a number from about 0.5 to about 5; and
   (b) subsequent neutralization wherein said neutralization is carried out at a pH of from about 5 to about 9.

2. The method according to claim 1, wherein $R^1$ represents an alkyl group having from about 12 to about 18 carbon atoms.

3. The method according to claim 1, wherein n is a number of from about 1 to about 2.

4. The method according to claim 2, wherein n is a number of from about 1 to about 2.

5. The method according to claim 1, wherein said sulfation is carried out with sulfur trioxide, wherein a mole ratio of fatty acid polyglycol ester to sulfur trioxide is from about 1:1 to about 1:3.

6. The method according to claim 2, wherein said sulfation is carried out with sulfur trioxide, wherein a mole ratio of fatty acid polyglycol ester to sulfur trioxide is from about 1:1 to about 1:3.

7. The method according to claim 3, wherein said sulfation is carried out with sulfur trioxide, wherein a mole ratio of fatty acid polyglycol ester to sulfur trioxide is from about 1:1 to about 1:3.

8. The method according to claim 4, wherein said sulfation is carried out with sulfur trioxide, wherein a mole ratio of fatty acid polyglycol ester to sulfur trioxide is from about 1:1 to about 1:3.

9. The method according to claim 1, wherein said sulfation is carried out nacontinuous falling-film reactor.

10. The method according to claim 4, wherein said sulfation is carried out in a continuous falling-film reactor.

11. The method according to claim 1, wherein said sulfation is carried out at a temperature of at least about 5° C. above the melting point of the fatty acid polyglycol ester.

12. The method according to claim 2, wherein said sulfation is carried out at a temperature of at least about 5° C. above the melting point of the fatty acid polyglycol ester.

13. The method according to claim 4, wherein said sulfation is carried out at a temperature of at least about 5° C. above the melting point of the fatty acid polyglycol ester.

14. The method according to claim 5, wherein said sulfation is carried out at a temperature of at least about 5° C. above the melting point of the fatty acid polyglycol ester.

15. The method according to claim 1, wherein said neutralization is carried out at a temperature of from about 10° C. to about 40° C.

16. The method according to claim 2, wherein said neutralization is carried out at a temperature of from about 10° C. to about 40° C.

17. The method according to claim 4, wherein said neutralization is carried out at a temperature of from about 10° C. to about 40° C.

18. The method according to claim 5, wherein said neutralization is carried out at a temperature of from about 10° C. to about 40° C.

19. A method of enhancing foam properties of surfactant mixtures, said method comprising:
   (a) providing a surfactant mixture;
   (b) providing a fatty acid polyglycol ester sulfate of the general formula (I):

$$R^1COO(AO)_nSO_3M \quad (I)$$

wherein $R^1CO$ represents a linear or branched, aliphatic, saturated and/or unsaturated acyl radical with 6 to 22 carbon atoms, AO represents $CH_2CH_2O$, $CHCH_3CH2O$ and/or $CH_2CHCH_3O$, n represents a number from about 0.5 to about 5 and M represents a cation; and
   (c) combining the surfactant mixture and the fatty acid polyglycol ester sulfate.

20. The method according to claim 19, wherein said surfactant mixture comprises a non-ionic surfactant.

* * * * *